United States Patent [19]

Crane et al.

[11] 4,373,787

[45] Feb. 15, 1983

[54] ACCURATE THREE DIMENSIONAL EYE TRACKER

[76] Inventors: Hewitt D. Crane, 25 Cordova Ct., Portola Valley, Calif. 94025; Carroll M. Steele, 1979 Scott La., Los Altos, Calif. 94022

[21] Appl. No.: 206,489

[22] Filed: Nov. 13, 1980

Related U.S. Application Data

[63] Continuation of Ser. No. 16,250, Feb. 28, 1979, abandoned.

[51] Int. Cl.³ .......................... A61B 3/14; A61B 3/10
[52] U.S. Cl. ................................ 351/210; 351/205; 351/211
[58] Field of Search ................ 351/1, 6, 7, 13, 16

[56] References Cited
U.S. PATENT DOCUMENTS

3,804,496  4/1974  Crane et al. .................. 351/6

*Primary Examiner*—John K. Corbin
*Assistant Examiner*—Rodney B. Bovernick
*Attorney, Agent, or Firm*—Urban H. Faubion

[57] ABSTRACT

A three dimensional eye tracker, for measuring as a function of time the point in three dimensional space on which the eye is fixed, includes a portion which functions as a two dimensional double Purkinje eye tracker for measuring movement of the eye in rotation and translation, an automatic optometer portion for measuring the refractive power of the eye, and a common optical path simultaneously to provide corrections for both portions of the instrument. The two dimensional eye tracker portion incorporates a means for directing a beam into the eye, thereby forming first and fourth Purkinje images, and measuring means responsive to the first and fourth Purkinje images to generate output signals indicative of eye rotation and translation. The automatic optometer portion alternately directs a light beam through different areas of the eye lens and includes a mechanism for altering the directed light beam until the image on the retina does not move. The common optical path for the light beams includes elements that stabilize the eye image in a way to make alignment of the subject in the instrument relatively easy and also to avoid errors both in measurement of refractive power and for direction of gaze due to translation and axial movement of the eye. Polarizers and mechanical stops are incorporated in the optometer portion to provide optical isolation between the eye tracker and the optometer portions, and electrical filtration is provided in both portions of the instrument further to avoid interference.

4 Claims, 2 Drawing Figures

FIG_1

FIG_2

ACCURATE THREE DIMENSIONAL EYE TRACKER

BACKGROUND OF INVENTION

The invention described herein was made in the course of work under a grant or award from the Department of Health, Education and Welfare.

This application is a continuation of Ser. No. 16,250 filed Feb. 28, 1979 now abandoned.

This invention pertains to a three dimensional eye tracker, and more particularly pertains to an eye tracker for continuously measuring the point in three dimensional space on which the eye is fixated. That is, the eye tracker continuously tracks orientation of the optic axis of the eye, movement of the eye along the axis, and also measures the dynamic refractive power of the same eye. The eye axis measurements are made by monitoring Purkinje images formed by reflecting surfaces within the eye. The refractive power measurements utilize a beam or beams alternately directed through different areas of the eye lens and monitors the movement of the image on the retina of the eye.

There are many areas of research as well as possibilities for commercial application in which it is desirable to have available electrical signals proportional to the orientation of the optic axis of a human observer's eye. Research on the mechanics of eye movement, on many areas of visual perception and on visual search patterns would all be greatly aided by such a device. Commercial applications include the use of the eye to control other systems. For example, a computer operator might simply look at any one of a number of symbols or locations displayed in front of him and press a button, introducing the value corresponding to that location into the computer. Similarly, a servo system for controlling a gun or camera could automatically be aimed at whatever object an observer visually was fixating.

The prior art contains many methods for attempting to track eye movement. These methods, their advantages and disadvantages are dealt with at length in three U.S. patents assigned to Stanford Research Institute, now known as SRI International, the assignee of the present patent application, said three patents all having as one of their inventors, Hewitt D. Crane, an inventor of the present application, as follows: U.S. Pat. No. 3,712,716 issued Jan. 23, 1973 to Tom N. Cornsweet and Hewitt D. Crane for "Eye Tracker", U.S. Pat. No. 3,724,932 issued Apr. 3, 1973 to Tom N. Cornsweet and Hewitt D. Crane for "Eye Tracker and Method", and U.S. Pat. No. 3,804,496 issued Apr. 16, 1974 to Hewitt D. Crane and Tom N. Cornsweet for "Two Dimensional Eye Tracker and Method for Tracking an Eye." Reference should be had to these patents for a discussion of the early trackers. The information is not repeated here, but the subject matter of those patents is specifically incorporated herein by reference.

The formation and characteristics of Purkinje images in the eye are also described in detail in the above referenced patents. Additionally, they are described in "Accurate Two-Dimensional Eye Tracker Using First and Fourth Purkinje Images" by T. N. Cornsweet and H. D. Crane, JOSA, v. 63, n. 8 (August 1973), pp. 921–928, and "Accurate Three-Dimensional Eyetracker" by H. D. Crane and C. M. Steele, App. Optics, v. 17, n. 5 (Mar. 1, 1978), pp. 691–705. In view of the full treatment of the subject of Purkinje images in these patents and articles, the information is not repeated here. The two articles, however, are also specifically incorporated herein by reference. Note also that the JOSA article describes a two dimensional Purkinje eye tracker and the Applied Optics article describes the present three dimensional Purkinje image eye tracker.

The two dimensional eye trackers disclosed and claimed in the above referenced patents have been highly successful and have solved many of the problems. For example, they do provide eye trackers which require no attachments to the eye, which produce tracking signals much more accurate than $\frac{1}{2}°$, and which are able to distinguish between translation artifacts and rotation of the eye. The eye trackers continuously monitor the orientation of the optic axis of the eye using first and fourth Purkinje images. As their designation indicates, however, the instruments only measure the direction of the visual axis and cannot accommodate axial variation in eye position.

An improved eye tracker which makes alignment of the subject even easier is disclosed in copending application Ser. No. 15,929, "Improved Double Purkinje Eye Tracker", filed Feb. 28, 1979 now U.S. Pat. No. 4,287,410 in the name of the present inventors and assigned to the assignee of the present invention. Alignment of the subject is easier because the eye tracker disclosed automatically makes allowance for axial eye movements and focuses Purkinje reflections from the eye of the subject as the eye is displaced or more axially. The eye tracker as described, however, does not measure the refractive power of the eye.

An instrument which does measure the refractive power of the eye is disclosed in the above referenced articles and also disclosed and claimed in U.S. Pat. No. 3,536,383 issued Oct. 27, 1970 to Tom N. Cornsweet and Hewitt D. Crane and assigned to the assignee of the present application. The automatic refractometer disclosed in the patent does not provide for measurements of the angle of gaze and does not include a way to compensate for transverse and axial displacement of the eye being refracted.

OBJECTS AND SUMMARY OF INVENTION

Accordingly, it is an object of this invention to provide a three dimensional eye tracker for measuring and tracking eye movements and automatically measuring the dynamic refractive power of the same eye.

It is another object of this invention to provide such a three dimensional eye tracker wherein allowance is also made for axial eye movements.

It is another object of this invention to provide a three dimensional eye tracker for refracting the eye and measuring eye movements by monitoring reflections from the eye which are focused in the eye tracker as the eye is displaced transversely or moved axially.

It is still another object of the invention automatically to provide such focus into the eye tracker mechanism regardless of refractive condition of the eye and also without changing the optical magnification or shifting the location of the images in the eye.

Briefly, in accordance with one embodiment of the invention, a three dimensional eye tracker is provided for tracking orientation of the optic axis of an eye, obtaining information relative to the position of the eye along its axis and automatically refracting the eye at the same time. Thus, the instrument measures the point in three dimensional space on which the eye is fixed at any given time. For obtaining information relative to the orientation of the optic axis of the eye and the displacement of the eye along its axis, a Purkinje image forming input beam is directed along a given axis to a fixed input mirror which directs the beam into the eye of a subject. Thus, a plurality of Purkinje images is formed by reflecting surfaces within the eye and reflected back into the eye tracker by the input mirror. A movable objective collimating lens directs the Purkinje images into the eye tracker mechanism, and two of the Purkinje images are monitored by providing deflecting means in series for imaging them on light flux measuring devices, or photodetectors. Servo systems are provided which are responsive to the photodetecting means for moving the deflecting means so that the Purkinje images are centered on their respective photodetectors. Therefore, monitoring orientation of the deflecting means gives an indication of where the eye is looking, i.e., the orientation of the optic axis of the eye. Focus of the images in the eye tracker mechanism is provided by incorporating a means to receive the beam from the said deflecting means and to focus the images nominally at a specific focal distance from the input and providing means to direct light from the beam a specific distance before and after the focal distance onto the surface of the light flux density measuring devices, which generate electrical signals. The difference of these signals, a measure of the condition of focus of the images, drives the movable objective collimating lens along an axis parallel to the axis of the input beam striking the fixed input mirror. In order to assure that the input light beam remains centered, a second movable deflecting means is fixed to the first of the series of deflecting means at a specific angle, so that it is redirected in fixed relation thereto. The refractive power of the eye is measured by directing a beam or beams of light alternately through different areas of the eye lens, detecting any movement of the beam image on the retina as the beams pass through different areas of the eye lens, and altering the incident light beam until the image does not move. Position and focus of the refracting beams are maintained by directing them onto the eye by way of the said second movable deflecting means and the said movable objective collimating lens. This is accomplished by inserting a beam splitter in the path of the refracting beams and also in the exit path of the Purkinje image containing beam (on the distal side relative to the eye).

The novel features which are believed to be characteristic of the invention are set forth with particularity in the appended claims. The invention itself, however, both as to its organization and method of operation, together with further objects and advantages thereof, may best be understood by reference to the following description taken in connection with the accompanying drawings.

BRIEF DESCRIPTION OF DRAWINGS

FIG. 2A is a detailed front view of the right angle mirror (182) of FIG. 2 used to direct the alternating beams into the subject eye;

FIG. 2B is a front view showing details of the stop (188) of FIG. 2 which is imaged onto the retina of the eye of the subject that effectively provides spacing of the incident alternately applied light beams;

FIG. 2C is a front view which illustrates the adjustable iris diaphragm 192 of FIG. 2; and FIG. 2D is a front view of the corneal stop 188 showing blocked Purkinje images.

DESCRIPTION OF PREFERRED EMBODIMENT

Figure 1:
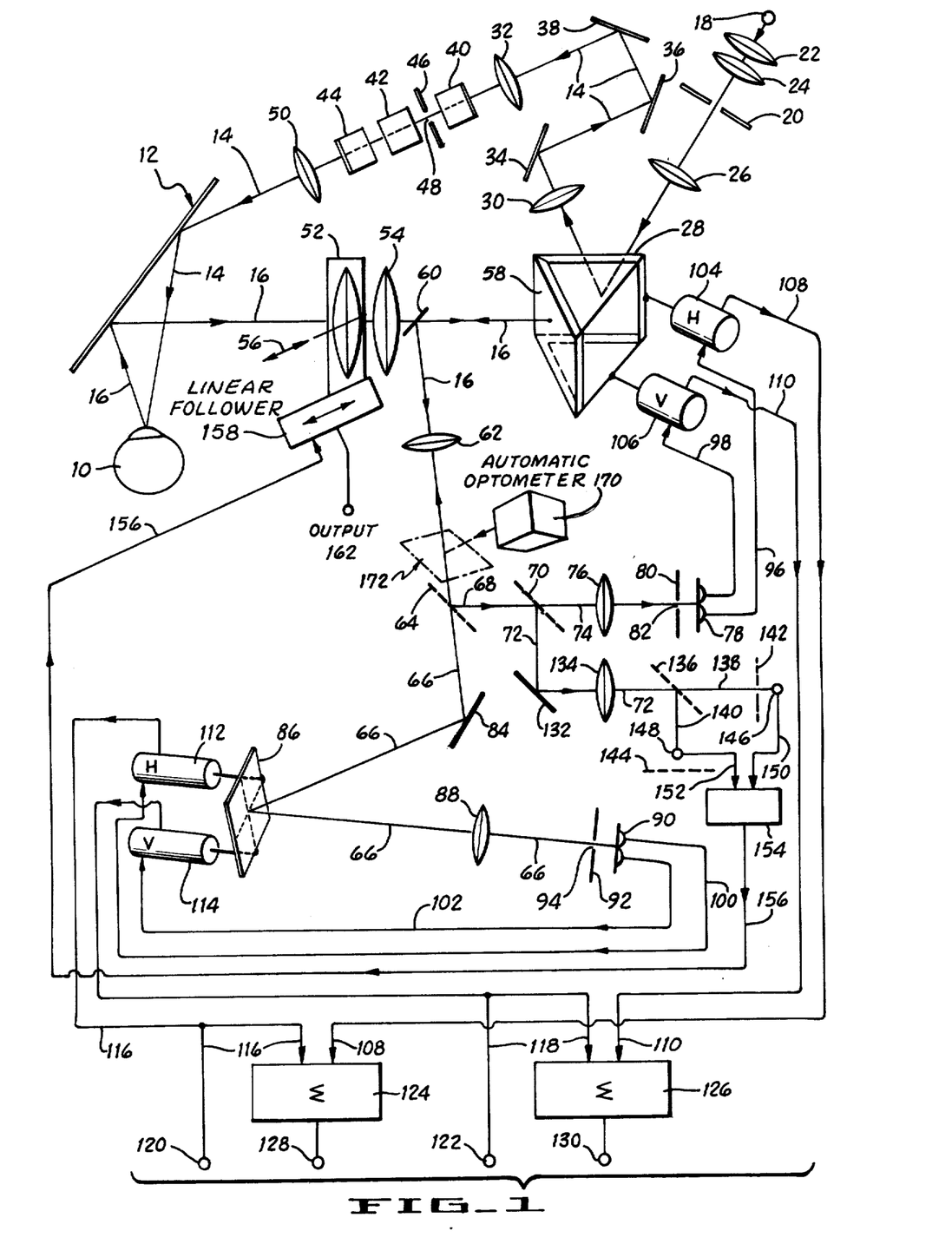
FIG. 1 is partially a perspective and partially a diagrammatic illustration of one embodiment of a three dimensional eye tracker.
Figure 2:
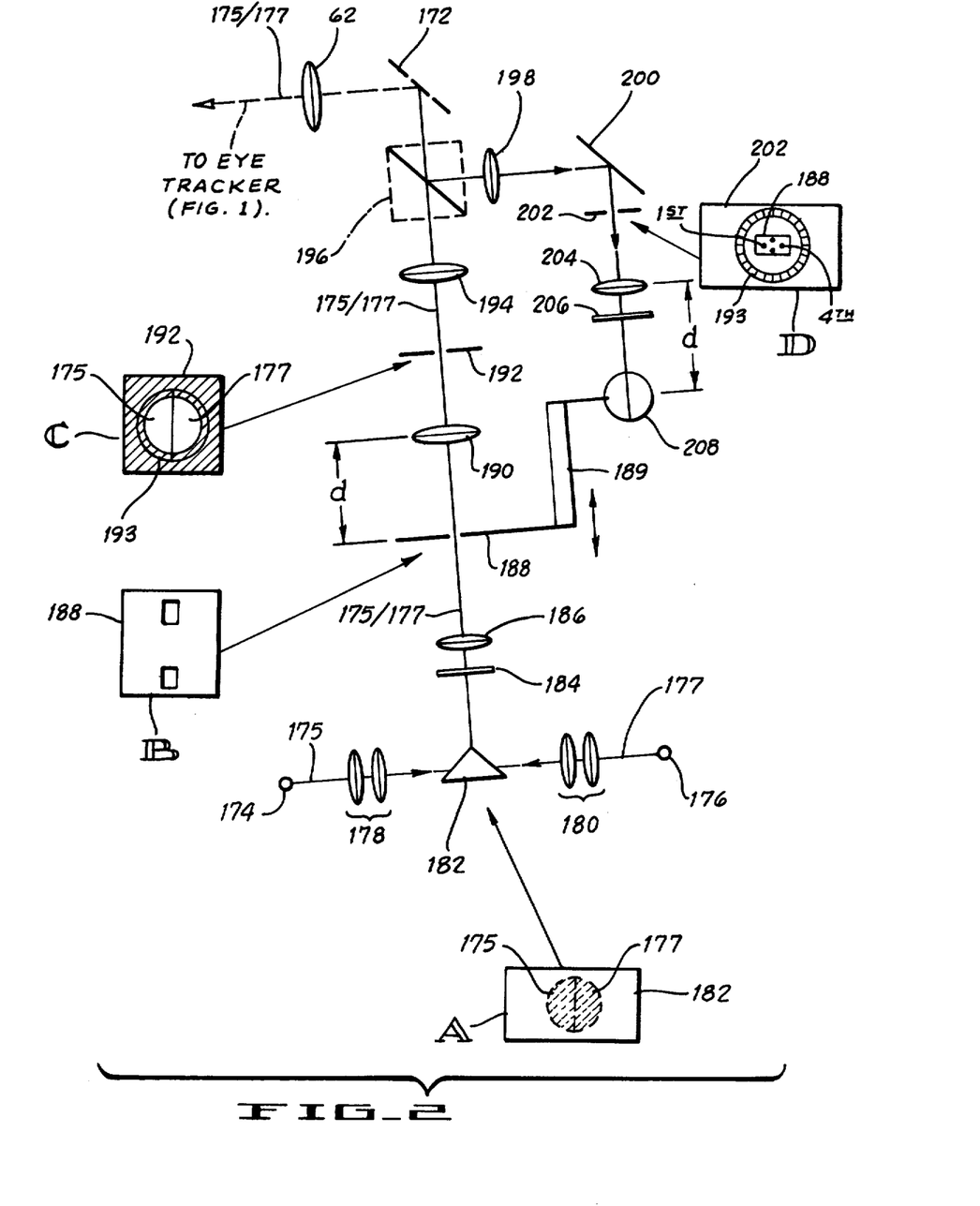
FIG. 2 is a diagrammatic illustration showing elements of the eye refracting part of the overall system.

The improved three dimensional eye tracker is illustrated in FIGS. 1 and 2. FIG. 2, however, illustrates the details of the refractometer portion of the system and the means of reducing interference between refraction and angle of eye axis measurements, and FIG. 1 is used to illustrate the details of measuring arrangements for the angle of eye axis and location of the eye along the eye axis. Both figures show how the overall combination goes together.

Measurement of angle of eye axis and determination of the location of the eye along the axis depend upon Purkinje images. As previously indicated, formation and location of Purkinje images are too well covered in the art for full description here. Since the first and fourth are important to the operation, however, a few words are in order.

As light passes through an eye, reflections occur at every interface at which there is a change in dielectric constant. There are, in particular, four surfaces where such reflections occur. The images formed by these reflections are well known and are generally referred to as Purkinje images. The virtual image of a light source that is formed by light reflected from front of the cornea is referred to as the first Purkinje image, or simply the corneal reflection. The fourth Purkinje image is formed by light reflected from the rear surface of the eye lens where the lens forms an interface with the vitreous humor that fills the bulk of the eyeball. This rear surface of the lens acts as a concave mirror, forming a real image of the source.

The fourth Purkinje image is almost the same size and is formed in almost exactly the same plane as the first Purkinje image, though it is over 100 times less intense. If the eye undergoes translation, such as a lateral head movement, both the first and fourth Purkinje images move together through the same distance and direction that the eye moves. If, on the other hand, the eye rotates either horizontally or vertically, the two images change their separation in space because the surfaces that form the first and fourth Purkinje images have centers of curvature that lie at different distances from the center of rotation of the eye. Referred to a fixed point in space, both images move in the direction of rotation of the eye, but they move by different amounts. The physical separation between these two images in space is a measure of the angular rotation of the eye in the direction of the shift, and the measure is nominally uncontaminated by lateral movements.

The improved double Purkinje image eye tracking system shown in FIG. 1 is identical to that described and claimed in copending patent application ACCURATE THREE DIMENSIONAL EYE TRACKER, Ser. No. 16,250 filed Feb. 28, 1979, now abandoned supra, except for the addition of the automatic optometer (refractometer) 170, which is introduced to provide the third dimension to the two dimensional eye tracker. In order to understand the synergistic cooperation between the parts of the instrument, it is necessary to understand full operation of the instrument. Therefore, a detailed description of the double Purkinje image system is given here.

The eye 10 of a subject is situated at some distance in front of a fixed input and reflecting dichroic mirror 12 which transmits visible and reflects infrared light. A display (not shown) is provided behind the dichroic mirror to present a visual field to the eye 10. The display may include a number of different areas to which the eye 10 may be visually directed, with the movements of the eye being tracked and used to initiate some control function. The infrared Purkinje images are formed in the eye 10 by incident infrared light beam 14, which is brought to the input mirror 12 on a fixed axis. The Purkinje images are reflected from the input mirror 12 into the eye tracker mechanism on Purkinje image beam 16.

Consider the formation of the input infrared light beam 14. A solid state light source 18 with a narrow spectral band centered at 0.93 μm wavelength generates the beam 14. Although not illustrated, in the practical eye tracker light from the source 18 is electronically chopped at high frequency (4 kHz) to avoid the effects of room light and to use ac coupled amplifiers in the Purkinje image servo systems, thereby improving stability and decreasing noise. The light source 18 is imaged onto the plane of an iris diaphragm 20, which is conjugate with the pupil of the subject's eye 10, by a pair of lenses 22 and 24. In order to collimate the light emerging from the iris 20, a collimating lens 26 is positioned one focal length therefrom. This collimated light is reflected from a gimbaled and servoed mirror 28 and imaged by lens 30. We assume for the moment that mirror 28 is fixed, and its structure and relation to other mirrors are ignored for now.

Another lens 32 is positioned one focal length from the image of the light source formed by lens 30, and the required path length (the sum of their focal lengths) between them is obtained by the multiple reflections provided by three mirrors 34, 36 and 38. The odd number of reflections (three) from these mirrors provides an inversion of the horizontal component of the input light path of beam 14. This inversion is necessary for the proper functioning of gimbaled input path mirror 28, by means of which, as described later, the input light beam 14 is made automatically to track any change in position of the eye 10. An inversion of the vertical component of the illumination beam 14 is also necessary for proper input light tracking. Therefore, there is another mirror system which includes three mirrors 40, 42 and 44, arranged in what may be termed a Dove mirror system. This name is used because the mirrors are arranged to function like a Dove prism, which keeps the axis of the exit beam the same as that of the input beam but provides an inversion.

In order to determine the size and shape of the Purkinje images formed at the eye 10, a stop 46 having a circular aperture 48 approximately 1 inch in diameter is provided within the Dove mirror system, between the first two mirrors 40 and 42. Light which is collimated with respect to the image of the aperture 48 is delivered to the eye 10 by inserting a lens 50 between the eye 10 and the stop 46, with its focal plane at both. Thus, the eye 10 is illuminated by the light coming from the light emitting diode 18. As previously indicated, stationary dichroic mirror 12 reflects both the illumination light on input beam 14 into the eye 10 and the light from the Purkinje images (including the first and fourth) that form in the subject's eye into the eye tracker on eye tracker input beam 16.

The Purkinje images are formed nominally in the pupil plane of the eye 10 which is in the focal plane of movable eye tracker mechanism objective lens 52. Thus light from the Purkinje images is collimated between objective lens 52 and the next adjacent focusing lens 54, which, as will be seen below, can also be considered an input focusing lens of the system, establishing a reference focal plane, or distance, for the focus control system. It also will be noted that eye tracker objective collimating lens 52 is mounted for movement off axis along arrows labeled 56 in the figure but with a component along its (the len's) axis. This action is for focusing, as is explained in more detail below.

Again following the Purkinje beam 16 back into the eye tracker, the light that passes through focusing lens 54 is reflected by a gimbaled image centering mirror 58 back onto a stationary mirror 60 which is in the focal plane of focusing lens 54. Lenses 52 and 54 have the same focal length and therefore provide a unity magnification image of the pupil plane of the eye 10 at stationary mirror 60. In order to extract and develop the information needed, it is necessary to divide, or split, the beam from the unity magnification image at stationary mirror 60 into a number of components. The best way to do this without distorting the image is to collimate the beam before splitting. Therefore, a collimating lens 62 is placed in the beam 16 reflected by mirror 60 a focal length away.

It will be noted here that the collimating lens 62 also affords an excellent optical position to merge the refractometer part 170 (automatic optometer 170) of the three dimensional eye tracker with the two dimensional angle of eye axis measuring part. This is done by introducing a conventional beam splitter 172 (referred to here as the refractometer beam splitter) on the distal side (from the eye 10) of the collimating lens 62 at an angle to deliver a beam from the refractometer 170 to the eye 10 (through collimating lens 62) and vice versa. The synergistic cooperation of the common optical portions of the system is discussed below. At this point follow the portion of the collimated light beam 16 which passes through the refractometer beam splitter 172 and is incident on Purkinje image beam splitter 64. This beam splitter (64) is so designated because the Purkinje images are used for the operations which take place in the part of the instrument which follows. Purkinje image beam splitter 64 passes about 90% of the beam 16 because the transmitted portion (66) of the beam 16 is used in connection with the weak fourth Purkinje image while the reflected 10% (68) is used in connection with the much stronger first Purkinje image.

Consider first the beam component 68 reflected at 90° by Purkinje image beam splitter 64. It is split again by beam splitter 70 which reflects (72) and transmits (74) approximately equal amounts of light. The transmitted light is imaged by focusing lens 76 onto the first Purkinje image four quadrant flux measuring device 78, which is in the focal plane of focusing lens 76. Light flux measuring device 78 is, therefore, in a plane conjugate to mirror 60 and, therefore, also in a plane conjugate to the pupil plane of the eye 10.

The light (beam 66) which passes through beam splitter 64 to a front surface mirror 84 is reflected onto a gimbaled and servoed mirror 86. Light reflected from gimbaled mirror 86 is collected by focusing lens 88 and focused at a second four quadrant light flux measuring device 90.

The four quadrant first Purkinje light flux measuring device 78 is provided with a stop plate 80 having an aperture 82 therein. In a similar fashion, four quadrant light flux measuring device 90 is provided with a stop plate 92 having an aperture 94 therein. The apertured plate 80 serves to mask the multiple quadrant photodetector 78 from the fourth Purkinje image but allows the first Purkinje image to pass through the aperture 82 to the light flux measuring device 78. Similarly, the apertured plate 92 serves to mask the light flux measuring device 90 from the first Purkinje image, allowing the fourth Purkinje image to impinge on the multiple quadrant photodetector 90 through the aperture 94.

The centers of the four quadrants of light flux measuring devices 78 and 92 are aligned with the apertures 82 and 94 in the first and fourth Purkinje image stop plates 80 and 92, respectively, and produce electrical output signals proportional to a shift of the incident beam from the centers of the quadrants. That is, the light flux measuring devices 78 and 90 generate electrical outputs on their electrical output circuits indicative of the position imbalance of the images falling thereon with respect to the four quadrants of the photodetectors. For example, as imbalance between the upper two quadrants and lower two quadrants of a photodetector is an indication that the image falling thereon is shifted with respect to the photodetector in a vertical direction. Similarly, an imbalance between the right and left pairs of quadrants of a photodetector is an indication that the image falling on the photodetector is shifted in a horizontal direction with respect to the axis of the photodetector. Thus, the first Purkinje image photodetector 78 produces a horizontal error signal at its horizontal error output circuit 96 in response to any horizontal imbalance and a vertical error signal on circuit 98 in response to any vertical imbalance. In like manner, fourth Purkinje image photodetector 90 produces error signals on circuits 100 and 102 in response to horizontal and vertical imbalances, respectively.

Gimbaled Purkinje image reflecting mirror 58 is pivoted by a pivot assembly to rotate about both vertical and horizontal axes. That is, the mirror 58 is rotatable in yaw around a vertical axis and in pitch around a horizontal axis. A horizontal servo system 104 is provided for rotating the mirror 58 in a horizontal direction (i.e., about its vertical axis) and a vertical servo system 106 is provided for rotating the mirror 58 in a vertical direction (i.e., about its horizontal axis). The horizontal servo system 104 receives as an input the position information on the electrical output circuit 96 of the multiple quadrant photodetector 78 as to the imbalance between its horizontal pairs of quadrants, which information corresponds to horizontal displacements of the first Purkinje image with respect to the multiple quadrant photodetector 78. The horizontal servo system provides an output signal on horizontal servo signal circuit 108 which depends upon the horizontal position of the first Purkinje image and is proportional to a combination rotation and translation of the eye 10. In a similar manner, the vertical servo system 106 receives input position information from the electrical output circuit 98 of the multiple quadrant photodetector 78 relative to the vertical imbalance between the vertical pairs of quadrants of the photodetector, which information corresponds to vertical movement of the first Purkinje image. Vertical servo system 106 produces a signal on its output circuit 110 depending upon the vertical position of the first Purkinje image.

When the first Purkinje image is at one particular point on mirror 60 (that is, in the pupil plane of the eye), it falls on the center of the four quadrant first Purkinje image light flux measuring device 78. If the image tends to move away from this point, the image at the photodetector 78 moves and the resulting error signals will drive servo motors 104 and 106 to reposition gimbaled image centering mirror 58 to bring the first Purkinje image to its initial point on stationary mirror 60, and thus on the photodetector. In this way, the image of the eye formed at stationary mirror 60 always has its corneal reflection in the same location. Also, by this arrangement Purkinje image reflecting mirror 58 maintains the first Purkinje image stationary on light flux measuring device 78, which is spatially fixed, and signals are generated indicative of both vertical and horizontal displacement of the first Purkinje image.

The fourth Purkinje image light flux measuring device, or photodetector, 90, as previously pointed out, functions simultaneously as a horizontally oriented split field cell and as a vertically oriented split field cell. Gimbaled fourth Purkinje image reflecting mirror 86 is pivoted by a pivot assembly to rotate about its central vertical and central horizontal axes. That is, the mirror 86 is pivoted at its center and is rotatable in yaw around a central vertical axis and in pitch around a central horizontal axis. A horizontal servo 112 is provided for rotating the mirror 86 in a horizontal direction (i.e., about its central vertical axis) and a vertical servo 114 is provided for rotating the mirror 86 in a vertical direction (i.e., about its central horizontal axis). Horizontal correction servo motor 112 is connected to receive the horizontal error signal (on circuit 100) generated by the photodetector 90, and vertical correction servo motor 114 is connected to receive the vertical error signal (on circuit 102). Thus, the fourth Purkinje image mirror 86 is driven so that the fourth Purkinje image is maintained in the center of the photodetector. In this manner fourth Purkinje mirror 86 is servo controlled to track movement of the fourth Purkinje image relative to the first Purkinje image.

If the eye 10 translates, the Purkinje image reflecting mirror 58 is automatically repositioned to maintain the first Purkinje image centered on the first Purkinje image photodetector 78. The same movement properly repositions the fourth Purkinje image at the center of the fourth Purkinje image photodetector 90, and therefore, no movement of the fourth Purkinje image positioning mirror 86 results. If the eye 10 rotates, however, the first and fourth Purkinje images move differentially and the proper horizontal and vertical signals are generated on the horizontal and vertical error circuits 100 and 102, respectively, to cause the horizontal and vertical servo motors 112 and 114 to reposition the fourth Purkinje image positioning mirror 86 so that the fourth Purkinje image is at the center of the four quadrant photodetector 90. Thus, the position of the fourth Purkinje image mirror 86 indicates the separation between the first and fourth Purkinje images at the pupil plane of the eye 10 and also is a measure of the two dimensional angular position of the eye 10. The horizontal and vertical servo motors 112 and 114, respectively, generate output signals which are a direct measure of the horizontal and vertical angular movement of the eye 10 and supply these outputs by way of circuits 116 and 118 directly to the horizontal and vertical rotational output terminals 120 and 122, respectively, and also to summing circuits 124 and 126 for processing.

The outputs at circuits 108 and 110, respectively, of the first Purkinje image horizontal and vertical servo motors 104 and 106 contain information relative to both eye translation and eye rotation (vertical and horizontal). This information, along with the outputs from fourth Purkinje image vertical and horizontal servo motors 114 and 112, which constitute a measure of the two dimensional angular position of the eye 10, contains all that is necessary to describe the orientation of the optic axis of the eye 10. Thus, the horizontal rotational signal on circuit 116 (from fourth Purkinje image horizontal centering servo 112) and the signal containing both horizontal rotational and translational information (on circuit 108) generated by first Purkinje image horizontal centering servo 104 are applied to a horizontal signal summing circuit which subtracts the rotational information to produce a pure horizontal translational output signal at its output terminal 128. In like manner, both the purely vertical rotational signal generated on output circuit 118 by fourth Purkinje image vertical servo motor 114 and the electrical signal generated by first Purkinje image vertical signal servo 106 on its output circuit 110 are applied to vertical translational summing circuit 126. The electrical signal on circuit 110 contains both vertical rotational and translational information. The summing circuit 126 subtracts the vertical rotational signal on circuit 118 to produce an output signal at its terminal 130 which contains purely vertical translational information. Thus, output terminals 120 and 122, respectively, provide pure horizontal and vertical rotational signals, and output terminals 128 and 130 of summing circuits 124 and 126, respectively, provide pure horizontal and vertical translational signals.

Note that the signals which drive the vertical servo motors 104 and 114 and horizontal servo motors 106 and 112 are generally referred to as error signals. The servo motors move until the error signals become zero. The error signals could themselves provide a direct measure of image movement without the servos, but in that form of system (generally referred to as open loop) the magnitude and the linearity of the output signals are very sensitive to factors such as component drift and change in gain in the photodetectors 78 and 90 and other circuit elements, variation in light sensitivity across the face of the photodetectors 78 and 90, and the uniformity, shape and brightness of the light pattern. The servo motors 104, 106, 112 and 114, by maintaining each image fixed at an electrically null position on their photodetectors, eliminate sensitivity to these parameters and result in a much more stable and accurate system.

Having discussed the way of signals defining eye axis orientation are derived, now consider the way a signal defining the focus of the Purkinje image delivered to the eye tracker mechanism is determined (i.e., information relative to the position of the eye in the direction of the input Purkinje image forming beam 14). Recall that the collimated beam incident on the beam splitter 70 is split, with half (beam 74) going to the first Purkinje image light flux measuring device 78 and half deflected downward (beam 72 in drawing). The light reflected downward from beam splitter 70 (beam 72) reflects from a front surface mirror 132 and is imaged by a focusing lens 134 which will focus the incident beam 72 at a given reference plane, or reference focal distance, at the focal plane of the lens. However, in order to obtain the focus information, another beam splitter 136 is used to divide the beam into two (50/50) components (138 and 140) of equal intensity which are nominally focused at focus reference planes 142 and 144 that are at the reference focal distance (the focal point of focusing lens 134).

Two focus detecting photodiodes 146 and 148 are displaced axially along beams 138 and 140, respectively, approximately 0.5 cm on either side of the reference focal distance, or reference planes of frame (142 and 144). Thus, the photodetectors 146 and 148, being small in size, measure light flux density along the axis of the imaging system, one photodetector 146 measuring light flux density behind the reference focal distance (at reference focal plane 142) and the other (photodetector 148) measuring the light flux density an equal distance in front of the reference focal distance (at reference focal plane 144). When the eye 10 is in the correct position axially, each of these photodetectors 146 and 148 receives the same amount of light, and therefore, they generate equal output signals on their respective output circuits 150 and 152. If the eye 10 moves axially, one or the other of these photodetectors receives more light, and the difference in light level causes the photodetectors 146 and 148 to generate different output signals on their output circuits 150 and 152. The photodetector on the same side of the reference focal distance with the point of focus generates the largest output signal. An error signal of proper sign and magnitude is obtained by connecting both output circuits to a comparator, or summing circuit, 154 which delivers a difference, or focus error, signal at its output circuit 156.

In the event a focus error signal is generated on the focus error output circuit 156, it is applied to a servo motor and linear follower 158 which repositions the eye tracker input focusing objective lens 52 to a point where the two focus error light flux density measuring devices 146 and 148 receive equal amounts of light. This ensures that the first Purkinje image is always in focus on the stationary mirror 60, and, consequently, first Purkinje image light flux measuring device 78, in spite of axial eye movement. Thus, the automatic focus system tracks the axial position of the eye to obtain the desired 1 cm of allowed axial variation in eye position. Without the automatic focus, intolerable blurring of the Purkinje images can occur at the first and fourth Purkinje image four quadrant light flux measuring devices 78 and 90, respectively.

It is noted that the eye tracker input objective lens 52 is driven (by its servo) along an axis 56 which is parallel to the axis of the input beam 14, not directly along its central axis. The central axis of the lens 52 is, however, maintained parallel to the eye tracker input light beam path 16 incident thereon. The reason for this arrangement is best understood by considering the focus system requirements.

The automatic focus system must meet two stringent requirements. First, any change is focus must not cause a change in optical magnification. A change in magnification would result in a change in separation of the two Purkinje images and, therefore, would be incorrectly interpreted as an eye rotation. Recall that the Purkinje images are in the focal plane of eye tracker objective lens 52 and that the light between lenses 52 and 54 is therefore collimated. Because the light is collimated, the eye 10 and objective lens 52 can both move along input light beam axis 16 without any change in magnification in the final image as long as the distance between the eye 10 and the objective lens 52 remains constant. The first step in automatic focus, therefore, is to have the axial position of objective collimating lens 50 track the axial position of the eye 10.

The second requirement of the automatic focus system is that the input light not shift if the eye 10 translates along the input light axis 14 (i.e., along the axis of the eye). If such an input light beam shift should take place while the input light beam 14 is already aimed directly at the eye 10, the shift would move the light source beam 14 away from the eye 10. In other words, the automatic focus system must be designed so eye translation along the input axis does not cause any shift in Purkinje image reflecting mirror 52, which, in turn, requires that there be no change in the position of the first Purkinje image. This is achieved by shifting eye tracker objective lens 52, not along its central axis (axis of incident beam 16), but along a path 56 parallel to the input light path 14 incident on the input reflecting mirror 12. Again, because the light between lenses 52 and 54 is collimated, an equal lateral component of shift of the eye 10 and objective lens 52 does not change the position of the final image formed by lens 54. A shift in eye position along any other axis will, however, shift the input light path appropriately as well as activate the automatic focus system.

Again recall that the signal (on circuit 156) that drives the focus servo system 158 derives from the difference in signals from focus light flux density measuring devices 146 and 148. This driving signal on circuit 156 is zero when the first Purkinje image is in focus at the reference focal distance and on first Purkinje image quadrant light flux measuring device 78. Output from the servo system that drives objective lens 52 is connected to its output terminal 162 and provides a direct measure of the axial position of the eye 10. Combined with the horizontal and vertical eye rotational position signals at output terminals 120 and 122, respectively, and vertical and horizontal eye translational position signals at output terminals 128 and 130 respectively, the three dimensional position of the globe (eye 10) can be accurately tracked.

As previously pointed out, the instrument is designed to permit up to a centimeter of eye position variation in all dimensions, horizontal, vertical and axial. For a large axial variation to be tolerated, it is necessary to incorporate automatic focus into the eye tracker (described immediately above). For large lateral variations to be tolerated, either a large input beam must be used, so the eye never moves out of the beam, or the input light path must track eye position automatically, in which case a small light source can be used. The latter option is the one chosen for this embodiment of the invention because it offers many advantages: less total light energy directed toward the eye, a crisper fourth Purkinje image because of less stray light, and improved automatic capture because the first Purkinje tracker can sometimes lock onto the iris if it is illuminated.

For automatic input path tracking, the gimbaled mirror 28 in the input light path 14 from the light source 18 is used to keep the illumination beam 14 centered on the pupil 10. For this purpose, the mirror 28 is rigidly connected to, and therefore moves in synchronism with, the Purkinje image reflecting mirror 58.

To understand how the input light is made to track eye position, note that if the eye moves upward, the corneal reflection tends to move upward on first Purkinje image photodetector 78. Error signals generated by the first Purkinje image photodetector 78, as described previously, reposition Purkinje image reflecting mirror 58 to maintain the corneal image centered on stationary Purkinje image reflecting mirror 60. Motion imparted to Purkinje image reflecting mirror 58, however, also repositions the gimbaled input light reflecting mirror 28; this automatically deflects the input illumination beam 14 upward to track the corneal reflection. The illumination tracking cannot be perfect with respect to the pupil of the eye because first Purkinje image photodetector 78 tracks the corneal reflection, which moves with respect to the eye pupil when the eye 10 makes rotational movements. Nevertheless, the design is such that the tracking error is less than 1 mm with eye translation of ±0.5 cm in any direction and with rotations of 15° in all directions (30° diameter field); that is, the input illumination beam tracks the center of the pupil to within 1 mm over this range.

A critical requirement of the input light tracking system is that a shift in the input light path 14 must not cause any change in the angle of the input axis (incident on the eye 10) with respect to the eye axis. Any such change alters the separation of the Purkinje images and, therefore, is incorrectly interpreted as an eye rotation. There are a number of ways to avoid this situation. For example, it is possible to achieve the desired input tracking by translating the iris diaphragm 20 in the source beam. Such a translation, however, requires yet another two dimensional servo system.

In the embodiment illustrated, the correct translation of the input beam 14 incident on the eye 10 is achieved by positioning input beam deflecting mirror 28 in the collimated light path between collimating lens 26 and imaging lens 30 and attaching it rigidly to Purkinje image reflecting mirror 58, as described above. The required movement sensitivity in the input light path 14 is obtained by the proper choice of angle between input beam deflecting mirror 28 and Purkinje image reflecting mirror 58.

It will be recognized from the above description that an instrument is provided which measures the point on which an eye is fixated as a function of time. Nothing is attached to the subject (patient), who is easily aligned in the device. The measuring wavelength is in the near infrared and is invisible. The usable field of the instrument is greater than 20°; the horizontal and vertical directions of gaze are measured with a noise level and repeatability of about 1 min of arc. The two dimensional instrument just discussed is described and claimed in our copending patent application "Improved Double Purkinje Eye Tracker", Ser. No. 15,929, filed Feb. 28, 1979. Two such instruments may be aligned side by side for tracking both eyes simultaneously. The third dimension is added by incorporating the refractometer 170 in the system.

In order to take advantage of the stabilization (both in focus and in location) of any image in the eye, the beam path 175/177 from the automatic optometer 170 is merged with the stabilizing portion of the eye tracker by inserting the beam splitter 172 in the optical path 16 of the two dimensional eye tracker mechanism. As previously stated, the merging beam splitter 172 is inserted on the distal side of the collimating lens 62 relative to the eye 10. In this manner the light beam 175/177, which is operative for refracting the eye 10, impinges upon the eye to form the required image or images in the eye, and the images are stabilized in location on the eye and also maintained in focus regardless of eye movements.

The principle of operation of the refractometer is based upon the fact that the focusing power of the eye can be determined by projecting a narrow beam through the eye lens and moving it back and forth across the lens while observing the image on the retina. If the image on the retina does not move, then the eye is focused at the distance at which the light source is placed. If the image on the retina moves in the same direction as the narrow beam, then the eye lens is not sufficiently strong (in refractive power), while if the image on the retina moves opposite to the direction of the movement of the narrow beam, then the eye lens is too strong. How the image on the retina moves is described and illustrated in great detail in both U.S. Pat. No. 3,536,383 and the Applied Optics article, supra. Therefore, this material is not repeated here, but in the embodiment of the invention illustrated (see FIG. 2) the movement of the narrow beam 175/177 is provided from two light sources 174 and 176 which are turned on and off in alternation.

In order to present alternating side-by-side beams 175 and 177 from the light sources 174 and 176 to the eye 10, they are imaged by lens pairs 178 and 180, respectively, onto a right angle mirror 182, which causes two half disks of light to appear side by side, as is best understood by considering the take-out view of FIG. 2A. This figure shows that half of each beam (175 and 177) strikes an opposite part (side) of the right angle mirror 182 at a 45° angle so that they are effectively reflected as side-by-side half disks, which are shown as a single beam (labeled with both reference numerals) because they are so close together. The fact is that they are so close together that they would appear as a single beam if the two sources 174 and 176 were energized simultaneously instead of alternately. Nevertheless, they do strike the eye lens in different places so that movement of the image on the retina can be observed. In this embodiment the light sources 174 and 176 are near-ir with a narrow spectral band centered at 0.93 micrometer ($\mu$m) wavelength and flicker on and off alternately at a rate of 400 Hz.

For orientation, observe that the combined beam 175/177 travels from right angle mirror 182 through a number of elements (which are ignored for now) and is directed into the eye 10 by way of the partially reflective mirror 172 and collimating lens 62. The beam splitting mirror 172 and collimating lens 62 are common to the full eye tracker mechanism. Recall that by merging the input beams on the distal side of collimating lens 62, as viewed from the eye 10, the beams benefit from the image stabilization (utilizing the first Purkinje image) by the gimbaled mirror 58.

Now consider the input light path from the right angle mirror 182 to the eye 10. The two half disks of light 175 and 177 are generated out of phase to form alternating beams. In order to be able to control the outside diameter of the light source pattern delivered at the pupil plane of the eye 10, an image of the flickering light pattern (175/177) is formed on a diaphragm 192 having an adjustable iris 193 by a pair of relay lenses 186 and 190 which are positioned between both the light images and the iris diaphragm 192. The first of the two lenses (186) is a focal length from the image of the flickering light 175/177.

A light polarizing element 184 is positioned in the just combined beam 175/177 adjacent and downstream of the right angle mirror 182, and a movable stop 188 is positioned in the beam 175/177 between the lens pair 186 and 190. The stop 188 is movable longitudinally along the axis of the beam 175/177 and is in fact the movable stop which is focused on the retina of the eye 10. The ability of the eye lens to focus the stop 188 on the retina when the position of the stop 188 is changed represents the accommodation level of the eye (measured in diopters). This point is discussed in more detail subsequently. The structure of the movable stop 188, best seen in the call-out FIG. 2B, constitutes a narrow slit with its center blocked. The reason for the center block is also discussed in more detail later.

Since relay lenses 186 and 190 are located a focal length from the image of the flickering light source, the combination relays the image to the plane of the adjustable iris diaphragm 192, where the diameter of the light source image is determined by adjusting the size of the iris 193 of the diaphragm 192. The structure of the adjustable iris diaphragm 192 and its relation to the flickering light images 175/177 is best seen in the front elevation call-out FIG. 2C.

A unity magnification image of the light source pattern 175/177 at the adjustable iris diaphragm 192 is delivered into the light path of the eye tracker portion of the system at the refractometer beam splitter mirror 172 by way of relay output lens 194. Since the lenses 190 and 194 are identical and separated by twice their focal length, they form a unity ratio relay lens which projects (relays) the image of the alternating light sources 174 and 176 (through collimating lens 62) on the stationary mirror 60 (FIG. 1). As explained above, the stationary mirror 60 is conjugate to the pupil plane of the eye 10, and therefore the size-adjusted image of the flickering light sources 174 and 176 is delivered to the pupil plane of the eye 10.

For an understanding of the operation of the refracting portion of the instrument is is important to note that the lens pair common to both light paths, comprising collimating lens 62 and focusing lens 54 (combination seen in FIG. 1), and the flickering light pattern delivering unity magnification lens pair 190 and 194 in the refracting light beam 175/177 (FIG. 2) are in series. A series pair of unity magnification relay lens pairs have the same linear properties as a single such lens pair. Therefore, with the stop 188 positioned so that its image is delivered to the focal plane of the first lens 62 in the relay pair 62 and 54, the light from the stop 188 reaching the lens pair (see FIG. 1) consisting of focusing lens 54 and objective lens 52 is collimated, and another image of the stop 188 is formed a distance of half the focal length of objective lens 52 from the pupil plane of the eye 10. This represents 9 diopters of refractive power. As the movable stop 188 is moved relative to the focal plane of the first lens 190 of its next adjacent relay lens pair 190 and 194, the final image moves correspondingly relative to the eye 10, i.e., to a position of more or less dioptric power. Note here that the linear relationship is maintained between eye diopters (magnification) and motion of movable stop 188.

The reason for blocking the center of the narrow slit of the movable stop 188 is that otherwise a very bright on-axis input light would be reflected directly back into the refractometer optics by the stationary mirror 60 (FIG. 1) after the folding reflection to gimbaled centering mirror 58 and then back (toward the focusing lens 54). Such a strong center reflection could cause a serious artifact in the refractometer measurement.

Having considered the refractometer input path and how the image is developed for causing the eye lens to change dioptric power, now consider the output path and the means for determining refractive power of the eye 10. Again note that the stationary mirror 60 (FIG. 1) is conjugate to the pupil plane of the eye 10. Also note that the functions of the beam positioning focusing and stabilization mechanism described earlier accrue to the optometer part of the system. The light beam path from the stationary mirror 60 back to the half reflective refractometer mirror 172 is the converse of (and consequently symmetrical to) the forward path already described, so the image of the stop 188 as it appears at the retina of the eye is reflected back (see FIG. 2) onto the surface of a reflecting and artifact eliminating polarizing beam splitter cube 196. Beam splitter cube 196, having its reflecting surface at a 45° angle, in turn reflects the beam in a path at a right angle to the input path to the first lens 198 in the optometer output path. The polarization of the polarizing beam splitter 196 is such that it passes the input beam 175/177 which was previously polarized by the input beam polarizing element 184 located just downstream of the beam combining right angle mirror 182 and also passes (back toward the input beam) specular reflections of the optometer input light beam 175/177 which can occur at surfaces of the lenses encountered and the cornea of eye 10. If these reflections were transmitted into the output path of the optometer, potentially large artifact signals could be generated.

The lens 198 which receives the light reflected by the polarizing beam splitter 196 is one of a relay pair (198 and 204) which are conjugate with the unity magnification relay lens pair 190 and 194, respectively, in the input beam path immediately following the stop 188 that is imaged on the retina of the eye 10. This being the case, the output lens 204 of the lens pair 198 and 204 in the output path relays an image of the light pattern which is formed on the retina to a conventional split field photocell 208. In order to fold the reflected light pattern so that it parallels the input flickering light beam 175/177, a mirror 200 is positioned at a 45° angle between the two lenses (198 and 204). Note also that a corneal stop 202 is located between the two lenses 198 and 204 of the relay systems and a polarizer 206 is positioned between the relay lens pair and the split field photocell 208. The function of each of these two elements is discussed below.

The stop 188 located in the input beam 175/177 and imaged at the retina of eye 10 and the split field photocell 208 are mechanically ganged (shown schematically by the link 189) so that they move together and are each the same variable distance "d", respectively, from lens 190 in the input beam 175/177 and the output lens 204 of the output relay pair (198 and 204). When the stop 188 is in focus on the retina of the eye 10, the retinal image is formed at a distance "d" from the output lens 204, and the light image so formed is stationary on the split field photocell 208. A stationary image centered on the split field photocell 208 produces an output signal from each half of the photocell which balances or cancels that from the other.

Any output from the split field photocell is used to drive a servo motor (not shown) that is connected to reposition the linkage mechanism 189 and thereby reposition the retinal image stop 188 and split field photocell 208 by the same amount. If the image of the stop 188 is out of focus on the retina, its image on the retina moves in synchronism with the flickering light sources 174 and 176 in one phase or the other and the output of the split field photocell 208 is such as to drive the mechanical linkage 189 (by drive motor and mechanism not shown) in the direction to produce a zero error signal at the split field photocell 208. The movement of the mechanism 189 provides an accurate measure of the refractive power of the eye. If the servo system has a faster response than the accommodation system of the eye 10, the instantaneous position of the mechanical link (or distance "d") provides an accurate measure of the instantaneous refractive power of the eye 10.

The corneal stop 202 in the output beam between the relay lens pair 198 and 204 is located in a plane conjugate with the iris 192 in the input beam and blocks Purkinje images produced by the eye tracker as well as those formed by input light from the optometer. The call-out FIG. 2D illustrates the location of various parts of the image and the stop blocking the first and fourth Purkinje images generated by the eye tracker light source 18 (labeled 1st and 4th) as well as those formed by the optometer light beam 175/177 (labeled 188). The beam splitting polarizer cube 196 prevents most of the optometer light that is reflected from the cornea from reentering the output path of the optometer. However, this reflected light is so bright that it is still necessary to use the corneal stop 202, that is large enough to block the corneal image of stop 188. By enlarging the stop, as shown in the call-out FIG. 2D, light from the first and fourth images from the eye tracker is also blocked. The stabilizing action of the eye tracker keeps the corneal reflection blocked by the corneal stop 202 even under conditions of eye rotation and/or translation.

As previously indicated, the beam splitter polarizer cube 196 blocks light from the input beam that would normally be reflected back into the output beam from the system lens surfaces because its polar orientation matches that of the light polarizer 184 which is provided in the input beam. However, because the cube 196 is not perfect, a certain amount of such light is scattered at its diagonal interface and from its rectilinear surfaces. The use of the additional polarizer 206 just after the output relay lens pair (198 and 204) significantly reduces the amount of scattered light.

A consideration of the above specification shows that the objects of the invention have been carried out by providing an accurate three dimensional eye tracker wherein the point in three dimensional space on which the eye 10 is fixated is continuously monitored. That is, the optic axis of the eye and dynamic refractive power of that eye are continuously tracked. In describing the invention a particular embodiment is shown. It will, of course, be understood that the invention is not limited thereto, since many modifications, both in the arrangements and instrumentalities employed, may be made. It is contemplated that the appended claims will cover any such modifications as fall within the true spirit and scope of the invention.

What is claimed is:

1. A three dimensional eye tracker for measuring, as a function of time, the point in three dimensional space on which the eye is fixed, including a two dimensional double Purkinje image eye tracker portion for measuring movement of the eye in rotation and translation, said eye tracker incorporating means for forming and directing a beam containing images of first and fourth Purkinje images, measuring means responsive to said first and fourth Purkinje images to generate output signals indicative of eye rotation and translation, optical focusing and positioning means positioned in the path of said images and responsive to said output signals to maintain the position of the first Purkinje image relative to the said eye and focus images from the eye, and an automatic optometer portion for measuring the refractive power of the eye, having beam generating means for forming an image at the eye and refractive power measuring means responsive to an image containing beam from the eye, at least a portion of said optometer beam path traversing a path including at least a portion of the said optical focusing and positioning means, whereby images formed by the said optometer portion are maintained in focus and stabilized in position.

2. A three dimensional eye tracker as defined in claim 1, wherein optical isolation means is provided for eliminating interference between beams formed in the said eye tracker and optometer portions and the means for generating output signals.

3. A three dimensional eye tracker for measuring, as a function of time, the point in three dimensional space on which the eye is fixed, including a two dimensional double Purkinje image eye tracker portion for measuring movement of the eye in rotation and translation, said eye tracker incorporating means for forming and directing an eye tracker input light beam to said eye, thereby forming first and fourth Purkinje images, means for forming and directing an eye tracker output beam containing the said first and fourth Purkinje images, optical image locating means adjustably positioned in both the said input and output beams for simultaneously stabilizing the position of the directed image on the eye and the position of the said output beam, optical image focusing means adjustably positioned in the said output beam to determine focus of the said images, Purkinje image location measuring means positioned to receive at least a portion of the said output beam from the said optical focusing means and image locating means, said Purkinje image location means being responsive to the said Purkinje images to generate output signals indicative of eye rotation and translation, image location determining servo means connected to receive the said output signals indicative of eye rotation and translation and connected to stabilize both the position of the directed image on the eye and the position of the said output beam, image condition of focus measuring means positioned to receive at least a portion of the said output beam from the said optical focusing means and image locating means and generate an output focus signal indicative of the condition of focus of at least one of the said images at a given location, image focus determining servo means connected to receive the said output focus signal indicative of the condition of focus of the said images and connected to reposition the said optical image focusing means in response to the said signal, thereby to focus the said images at the said given position, an automatic optometer portion for measuring the refractive power of the eye including optometer input light beam generating means for projecting a refracting image to the eye, and means for projecting an optometer output beam containing said image from the eye back into the said optometer, whereby a measure of the refractive power of the eye may be made, a portion of each said optometer input and output beams and the said eye tracker output beam having a common path with each other which includes the said optical image focusing means and the said image locating means, whereby the focus and location of the said refracting image at the eye and position of the output beam are thereby stabilized.

4. A three dimensional eye tracker as defined in claim 2, wherein optical isolation means is provided for eliminating interference between beams formed in the said eye tracker and optometer portions and the means for generating output signals.

* * * * *